United States Patent
Tenley et al.

(10) Patent No.: US 7,313,961 B2
(45) Date of Patent: Jan. 1, 2008

(54) METHOD AND APPARATUS FOR INSPECTING A COMPONENT

(75) Inventors: Brenda Catherine Tenley, Liberty Township, OH (US); Michael Leonard Dziech, Cincinnati, OH (US); Joseph Anthony Traxler, Fairfield Township, OH (US); James Michael Donovan, Ripley, OH (US)

(73) Assignee: General Electric Company, Schenectady, NY (US)

( * ) Notice: Subject to any disclaimer, the term of this patent is extended or adjusted under 35 U.S.C. 154(b) by 289 days.

(21) Appl. No.: 11/114,316

(22) Filed: Apr. 26, 2005

(65) Prior Publication Data

US 2006/0236769 A1    Oct. 26, 2006

(51) Int. Cl.
G01N 29/265 (2006.01)
G01N 29/26 (2006.01)
G01N 29/24 (2006.01)

(52) U.S. Cl. .......................................... 73/634; 73/640
(58) Field of Classification Search ................. 73/618, 73/633, 634, 635, 640
See application file for complete search history.

(56) References Cited

U.S. PATENT DOCUMENTS

| | | | | |
|---|---|---|---|---|
| 3,575,043 A | * | 4/1971 | Allen et al. ................... 73/619 |
| 4,018,082 A | * | 4/1977 | Manoliu et al. ............... 73/600 |
| 4,035,839 A | * | 7/1977 | Eggleton et al. ............... 73/618 |
| 4,083,232 A | * | 4/1978 | Heyser et al. ................. 73/618 |
| 4,194,400 A | | 3/1980 | Staff |
| 4,468,620 A | | 8/1984 | Vaerman |
| 4,644,274 A | | 2/1987 | Casarcia |
| 4,881,177 A | * | 11/1989 | McClean et al. ........... 700/258 |
| 5,315,234 A | | 5/1994 | Sutton, Jr. et al. |
| 5,442,285 A | | 8/1995 | Zombo et al. |
| 5,781,007 A | | 7/1998 | Partika et al. |
| 6,658,939 B2 | * | 12/2003 | Georgeson et al. ........... 73/621 |
| 6,792,809 B1 | * | 9/2004 | Moore .......................... 73/618 |
| 2004/0139802 A1 | * | 7/2004 | Gripp ........................... 73/633 |
| 2006/0048579 A1 | * | 3/2006 | Haase et al. .................. 73/618 |

* cited by examiner

Primary Examiner—Hezron Williams
Assistant Examiner—Rose M Miller
(74) Attorney, Agent, or Firm—William Scott Andes; Armstrong Teasdale LLP

(57) ABSTRACT

A method for inspecting a gas turbine engine component includes positioning an ultrasonic probe assembly proximate to a surface of the component, wherein the ultrasonic probe assembly includes a body portion and an inspection bar, coupling the inspection bar to the body portion such that the inspection bar is substantially vertical with respect to the body portion, moving the ultrasonic probe assembly along a substantially horizontal axis while generating ultrasonic data of the component, coupling the inspection bar to the body portion such that the inspection bar is substantially horizontal with respect to the body portion, moving the ultrasonic probe assembly along a substantially vertical axis while generating ultrasonic data of the component, and utilizing the generated data to reconstruct an image of the component.

20 Claims, 8 Drawing Sheets

METHOD AND APPARATUS FOR INSPECTING A COMPONENT

BACKGROUND OF THE INVENTION

This invention relates generally to non-destructive testing and, more particularly, to ultrasound inspection of fabricated components.

Ultrasonic inspection techniques are used in many applications where non-destructive evaluation of a workpiece or component is required. One application of such ultrasonic inspection is in the inspection of gas turbine engine components. Such components are typically formed from a forging of a material with desired metallurgical properties, and may include a relatively complex geometry.

However, at least some known ultrasonic inspection systems include an ultrasonic probe that is coupled to a relatively large support structure. At least some known support structures are relatively heavy such that an operator may experience difficulty in manipulating the inspection system while inspecting the component and/or maintaining the inspection system normal to the surface of the component under test. Moreover, due to their relatively large size, known ultrasonic inspection systems cannot be utilized to test components that are positioned in a more restrictive space.

Moreover, during an inspection procedure, at least some known ultrasonic inspection devices are randomly manipulated by an operator over the surface of the component until the testing procedure is completed. However, randomly manipulating an ultrasonic testing system during the test procedure may result in a failure to test certain portions of the component under test.

Accordingly, known ultrasonic inspection devices may be less effective in generating an accurate representation of the component when the component is positioned in a more restrictive environment, and/or when the component has a relatively complex geometry such that the probe cannot be consistently placed normal to the surface of the component during the scan procedure.

BRIEF DESCRIPTION OF THE INVENTION

In one aspect, a method for inspecting a gas turbine engine component is provided. The method includes positioning an ultrasonic probe assembly proximate to a surface of the component; said ultrasonic probe assembly including a body portion and an inspection bar, coupling the inspection bar to the body portion such that the inspection bar is substantially vertical with respect to the body portion, moving the ultrasonic probe assembly along a substantially horizontal axis while generating ultrasonic data of the component, coupling the inspection bar to the body portion such that the inspection bar is substantially horizontal with respect to the body portion, moving the ultrasonic probe assembly along a substantially vertical axis while generating ultrasonic data of the component, and utilizing the generated data to reconstruct an image of the component.

In another aspect, an ultrasonic probe assembly for inspecting a component is provided. The ultrasonic probe assembly includes a substantially U-shaped body portion comprising a first portion, a second portion, and a third portion coupled to the first and second portions, an ultrasonic transmitter coupled to a first end of the body portion and configured to transmit a plurality of ultrasonic waves through the component under test, an ultrasonic receiver coupled to a second end of the body portion configured to receive at least a portion of the ultrasonic waves transmitted through the component under test, and, a data acquisition system configured to receive data from the ultrasonic receive and reconstruct an image of the component under test.

DETAILED DESCRIPTION OF THE INVENTION

Figure 1:
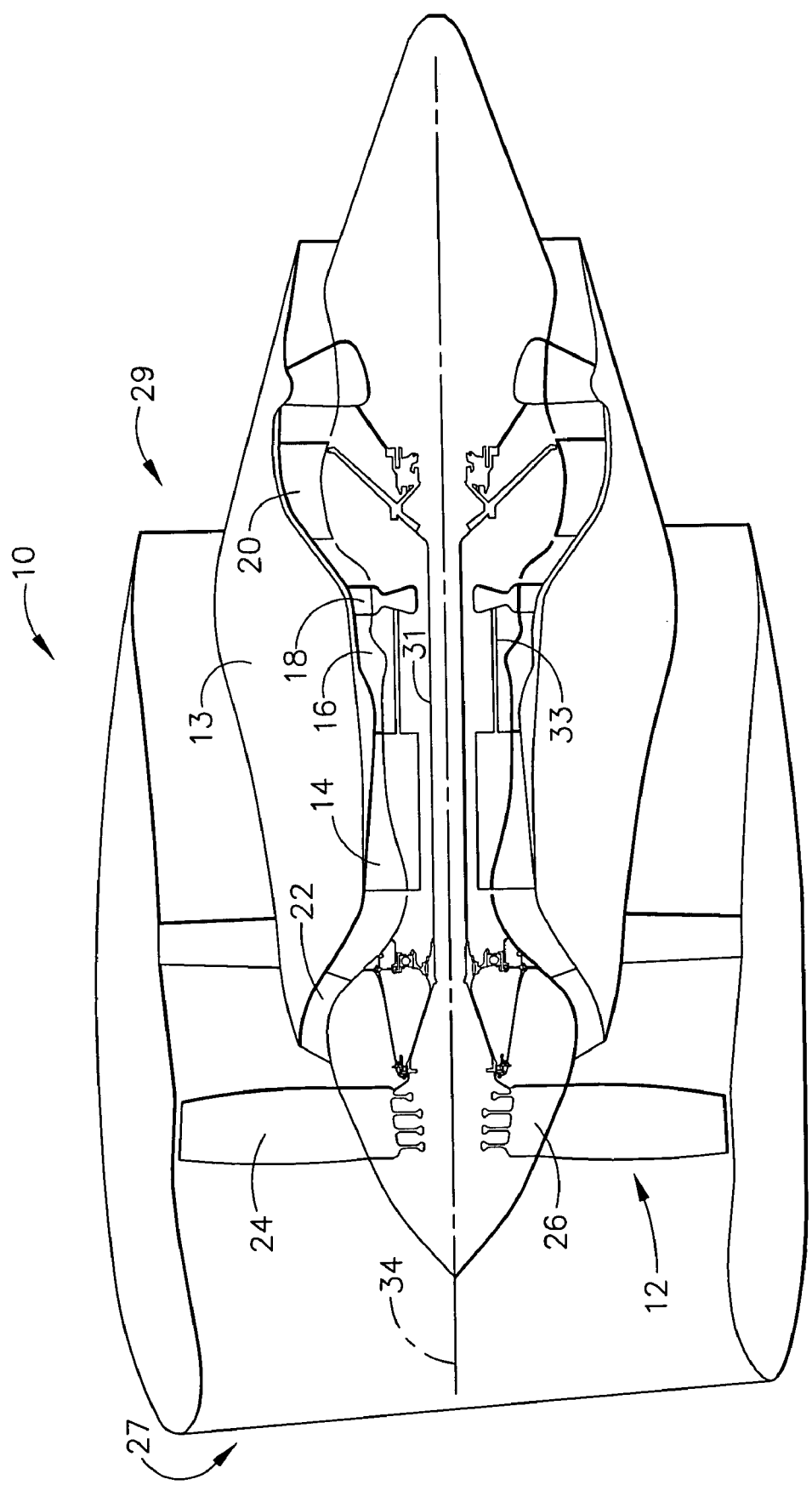
FIG. 1 is a schematic illustration of an exemplary gas turbine engine.

FIG. 1 is a schematic illustration of an exemplary gas turbine engine 10 including a fan assembly 12 and a core engine 13 including a high pressure compressor 14, and a combustor 16. Engine 10 also includes a high pressure turbine 18, a low pressure turbine 20, and a booster 22. Fan assembly 12 includes an array of fan blades 24 extending radially outward from a rotor disc 26. Engine 10 has an intake side 27 and an exhaust side 29. In one embodiment, the gas turbine engine is a GE90-115B that is available from General Electric Company, Cincinnati, Ohio. Fan assembly 12 and turbine 20 are coupled together using a first rotor shaft 31, and compressor 14 and turbine 18 are coupled together using a second rotor shaft 33.

During operation, air flows axially through fan assembly 12, in a direction that is substantially parallel to a central axis 34 extending through engine 10, and compressed air is supplied to high pressure compressor 14. The highly compressed air is delivered to combustor 16. Airflow (not shown in FIG. 1) from combustor 16 drives turbines 18 and 20, and turbine 20 drives fan assembly 12 by way of shaft 31.

Figure 2:
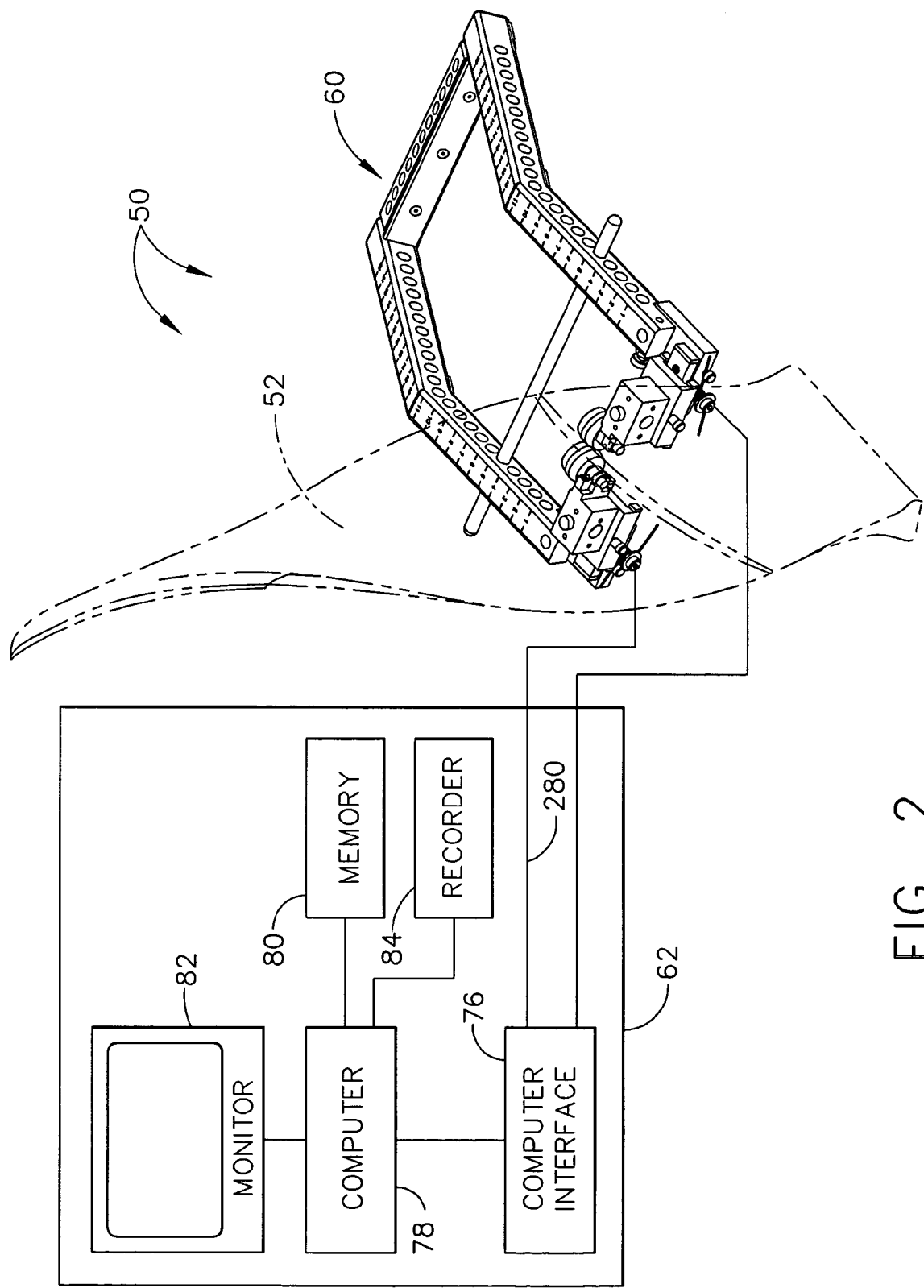
FIG. 2 is a schematic diagram of an exemplary ultrasonic inspection system that includes an ultrasonic probe assembly.

FIG. 2 is a schematic diagram of an exemplary ultrasonic flaw detection system 50 that can be used to inspect a component 52 such as, but not limited to, fan blade 24 (shown in FIG. 1). Although the methods and apparatus herein are described with respect to fan blade 24, it should be appreciated that the methods and apparatus can be applied to a wide variety of components. For example, component 52 may be of any operable shape, size, and configuration. Component 52 may be fabricated of any operable base material such as, but not limited to, nickel-base alloys, cobalt-base alloys, titanium-base alloys, iron-base alloys, and/or aluminum-base alloys. More specifically, although the methods and apparatus herein are described with respect to aircraft engine parts, it should be appreciated that the methods and apparatus can be applied to inspect components used within a steam turbine, a nuclear power plant, or to inspect a wide variety of other mechanical components. In the exemplary embodiment, detection system 50 includes a probe assembly 60 and a data acquisition/ control system 62. Probe assembly 60 is electrically coupled to data acquisition/control system 62 such that data generated by probe assembly 60 can be transmitted to data acquisition/control system 62.

In the exemplary embodiment, data acquisition/control system 62 includes a computer interface 76, a computer 78, such as a personal computer with a memory 80, and a monitor 82. Computer 78 executes instructions stored in firmware (not shown). Computer 78 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Memory 80 is intended to represent one or more volatile and/or nonvolatile storage facilities that shall be familiar to those skilled in the art. Examples of such storage facilities often used with computer 78 include, but are not limited to, solid state memory (e.g., random access memory (RAM), read-only memory (ROM), and flash memory), magnetic storage devices (e.g., floppy disks and hard disks), and/or optical storage devices (e.g., CD-ROM, CD-RW, and DVD). Memory 80 may be internal to or external to computer 78. Data acquisition/control system 62 also includes a recording device 84 such as, but not limited to, a strip chart recorder, a C-scan, and an electronic recorder, that is electrically coupled to either computer 78 and/or ultrasonic probe assembly 60.

Figure 3:
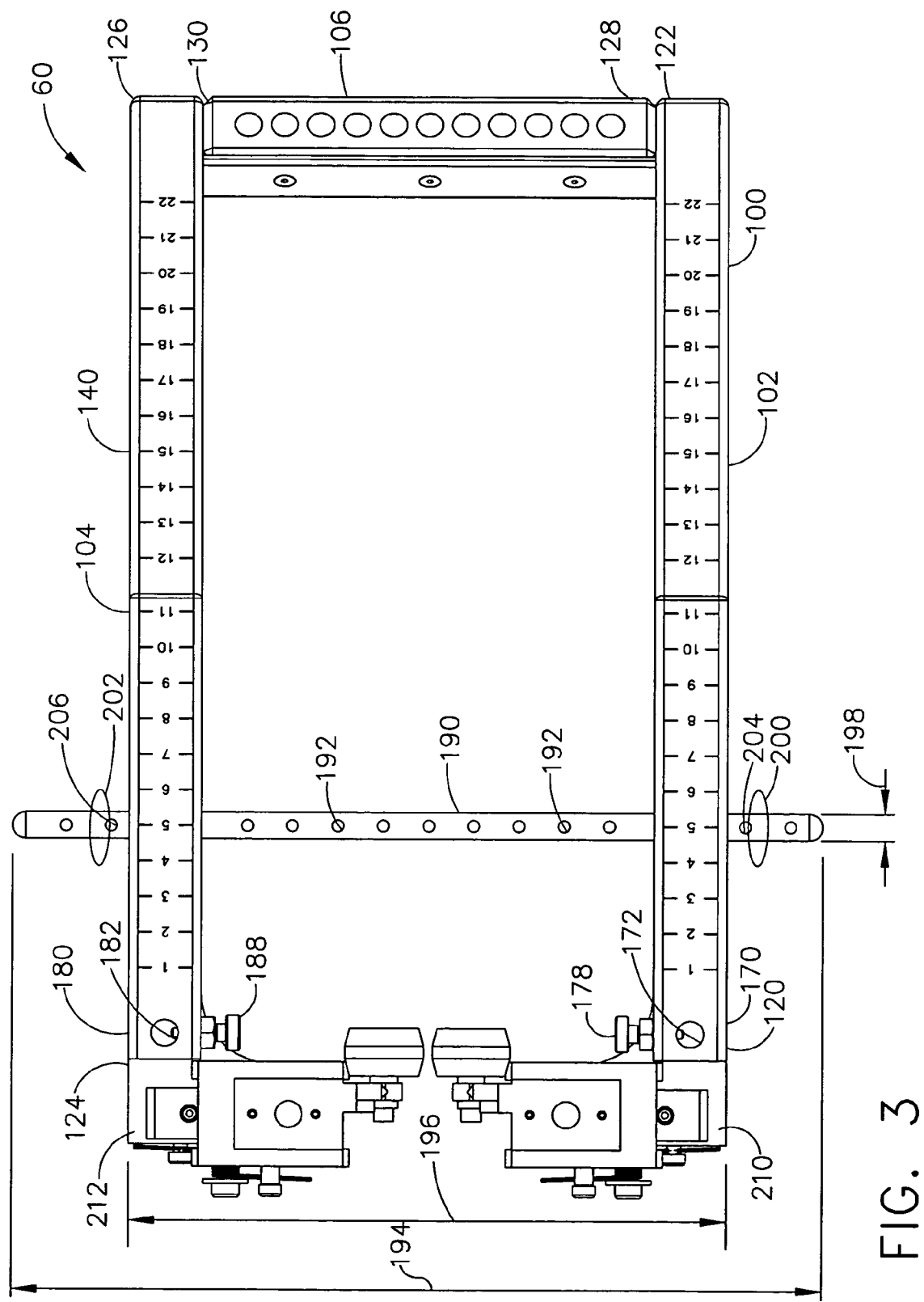
FIG. 3 is a top plan view of the probe assembly shown in FIG. 2.
Figure 4:
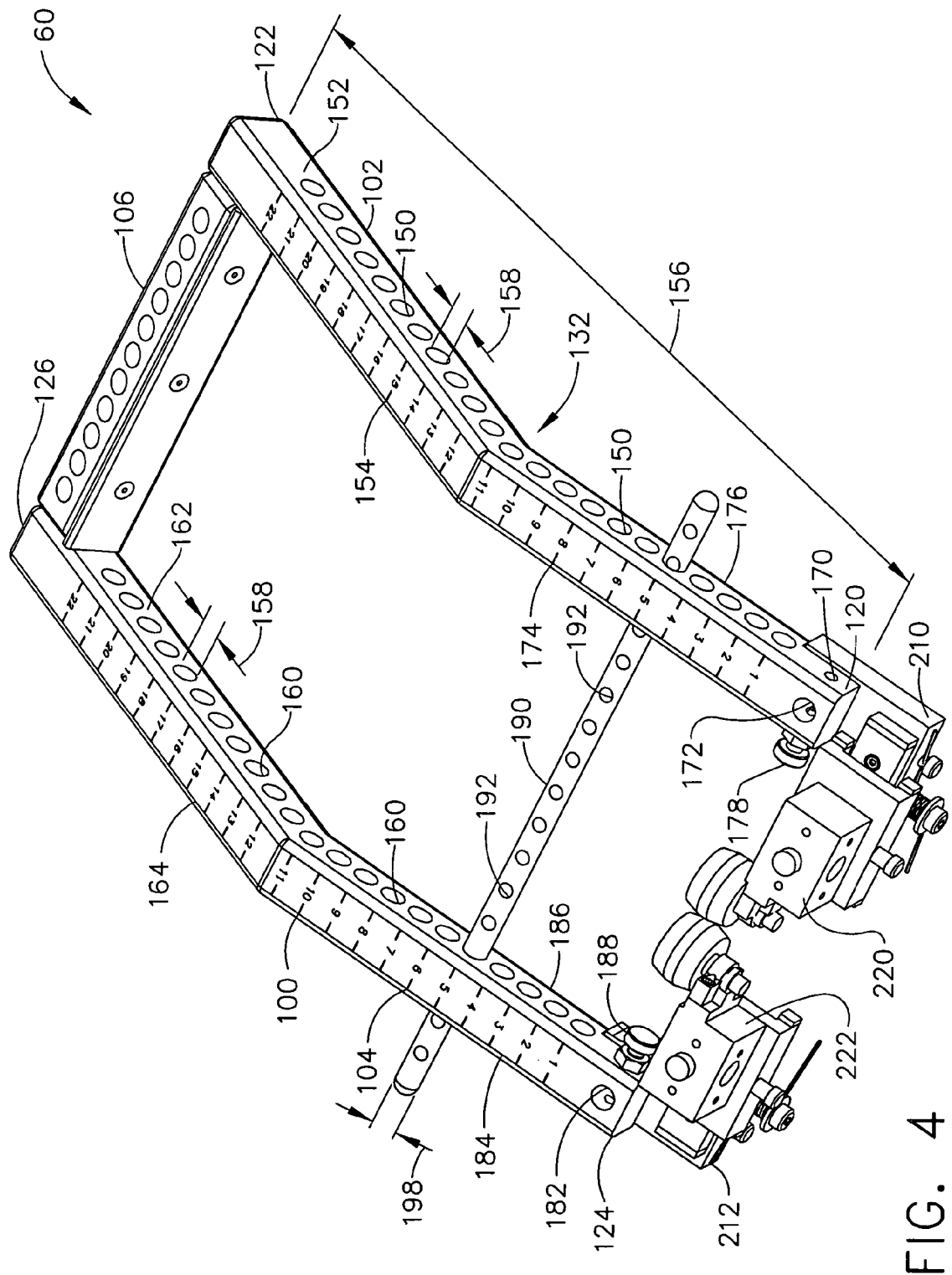
FIG. 4 is a top perspective view of the probe assembly shown in FIG. 2.
Figure 5:
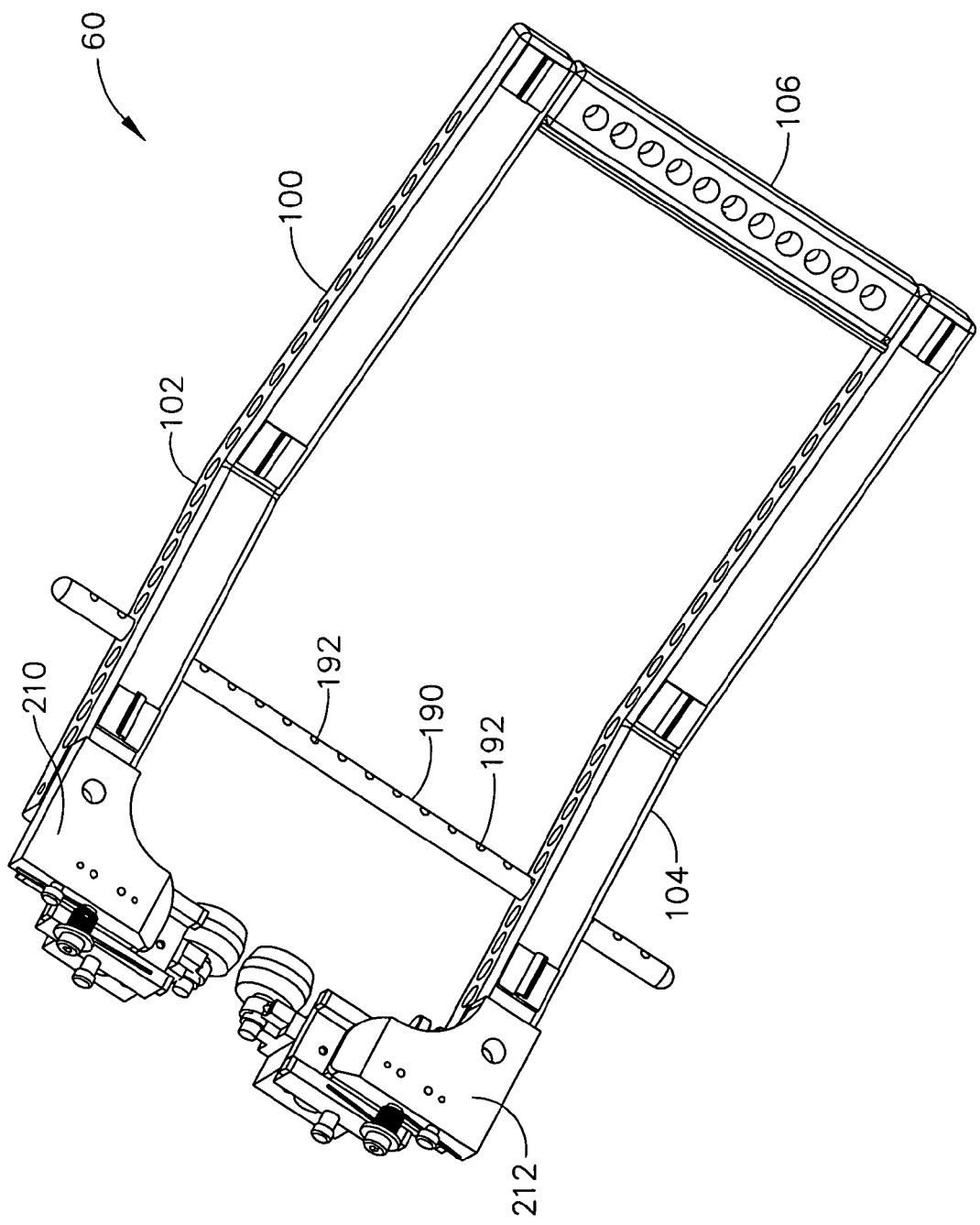
FIG. 5 is a bottom perspective view of the probe assembly shown in FIG. 2.

FIG. 3 is a top plan view of probe assembly 60. FIG. 4 is a top perspective view of probe assembly 60. FIG. 5 is a bottom perspective view of probe assembly 60. In the exemplary embodiment, probe assembly 60 includes a body 100 that includes a first portion 102, a second portion 104, and a third portion 106 that is coupled between first and second portions 102 and 104, respectively. First, second, and third portions 102, 104, and 106 are coupled to together such that body 100 has a substantially U-shaped profile. More specifically, first portion 102 includes a first end 120 and a second end 122, second portion 104 includes a first end 124 and a second end 126, and third portion 106 includes a first end 128 and a second end 130. During assembly, first portion second end 122 is coupled to third portion first end 128, and second portion second end 126 is coupled to third portion second end 130 such that body 100 has a substantially V-shaped cross-sectional profile 132 to facilitate use of probe assembly 60 as discussed herein.

In the exemplary embodiment, body 100 is fabricated from a relatively light weight metallic material 140, such as aluminum, for example, to facilitate reducing the weight of probe assembly 60. In an alternative embodiment, body 100 is fabricated using a relatively lightweight material other than metal such as, but not limited to, a fiberglass material and/or a plastic material, for example. In the exemplary embodiment, material 140 has a substantially square cross-sectional profile. In an alternative embodiment, material 140 has a cross-sectional profile that is not substantially square, such as circular, for example.

First portion 102 includes a plurality of openings 150 that extend from a first side 152 to a second side 154 of first portion 102. In the exemplary embodiment, plurality of openings 150 are approximately equidistantly spaced in one inch increments along a length 156 of first portion 102. Moreover plurality of openings 150 each have an inside diameter 158 that are each sized to receive an inspection bar 190. Second portion 104 includes a plurality of openings 160 that extend from a first side 162 to a second side 164 of second portion 104. In the exemplary embodiment, plurality of openings 160 are approximately equidistantly spaced in one inch increments along length 156. Moreover plurality of openings 160 each have an inside diameter 158 that are each sized to receive inspection bar 190.

First portion 102 also includes an opening 170 that is positioned proximate to first end 120 and extends horizontally from first side 152 to second side 154 of first portion 102, and an opening 172 that is positioned proximate opening 170 and extends vertically from a first portion upper surface 174 to a first portion lower surface 176. In the exemplary embodiment, a retaining pin 178 is inserted at least partially into opening 170 to facilitate securing inspection bar 190 therein. In one embodiment, retaining pin 178 includes a spring (not shown) such that retaining pin 178 is "spring loaded" into opening 170. More specifically, when retaining pin 178 is moved in a first direction, the spring forces tension against retaining pin 178, when retaining pin 178 is released, the spring forces retaining pin 178 at least partially through opening 170 to facilitate securing retaining pin 178 at least partially within opening 170, and thus securing inspection bar 190 within opening 172.

Second portion 104 also includes an opening 180 that is positioned proximate to first end 124 and extends horizontally from first side 162 to second side 164 of second portion 104, and an opening 182 that is positioned proximate opening 180 and extends vertically from a second portion upper surface 184 to a second portion lower surface 186. In the exemplary embodiment, a retaining pin 188 is inserted at least partially into opening 180 to facilitate securing inspection bar 190 therein. In one embodiment, retaining pin 188 includes a spring (not shown) such that retaining pin 188 is "spring loaded" into opening 180. More specifically, when retaining pin 188 is moved in a first direction, the spring forces tension against retaining pin 188, when retaining pin 188 is released, the spring forces retaining pin 188 through opening 180 to facilitate securing retaining pin 188 at least partially within opening 180, and thus securing inspection bar 190 within opening 182.

Ultrasonic probe assembly 60 also includes at least one inspection bar 190 that includes a plurality of openings 192. In the exemplary embodiment, inspection bar 190 has a length 194 that is greater than a width 196 of body 100. In the exemplary embodiment, inspection bar 190 has a diameter 198 that is smaller than diameter 158 of openings 160, respectively. More specifically, inspection bar 190 is sized such that it can be inserted through first plurality of openings 150 and then through second plurality of openings 160. Accordingly, and in the exemplary embodiment, inspection bar 190 has a length 194 that is greater than a width 196 of body 100 such that inspection bar 190 is facilitated to remain coupled to body 100 during an inspection procedure. In one embodiment, inspection bar 190 includes a first coupling device 200 such as a clip, for example, and a second coupling device 202 to facilitate securing inspection bar 190 to body 100 after inspection bar 190 has been inserted through first and second plurality of openings 150 and 160 respectively. For example, during one exemplary operation, inspection bar 190 is inserted through first opening 150, and through second opening 160. First clip 200 is inserted through a first opening 204 in inspection bar 190, and second clip 202 is inserted through a second opening 206 in inspection bar 190 to facilitate securing inspection bar 190 to body 100.

Probe assembly 60 also includes a first sensor mounting plate 210 and a second sensor mounting plate 212. In the exemplary embodiment, first and second mounting plates 210 and 212 are substantially L-shaped and are coupled to first and second portions 102 and 104, respectively. Probe assembly 60 also includes a ultrasonic transmitter assembly 220 that is coupled to first mounting plate 210, and an ultrasonic receiver assembly 222 that is coupled to second mounting plate 212.

Figure 6:
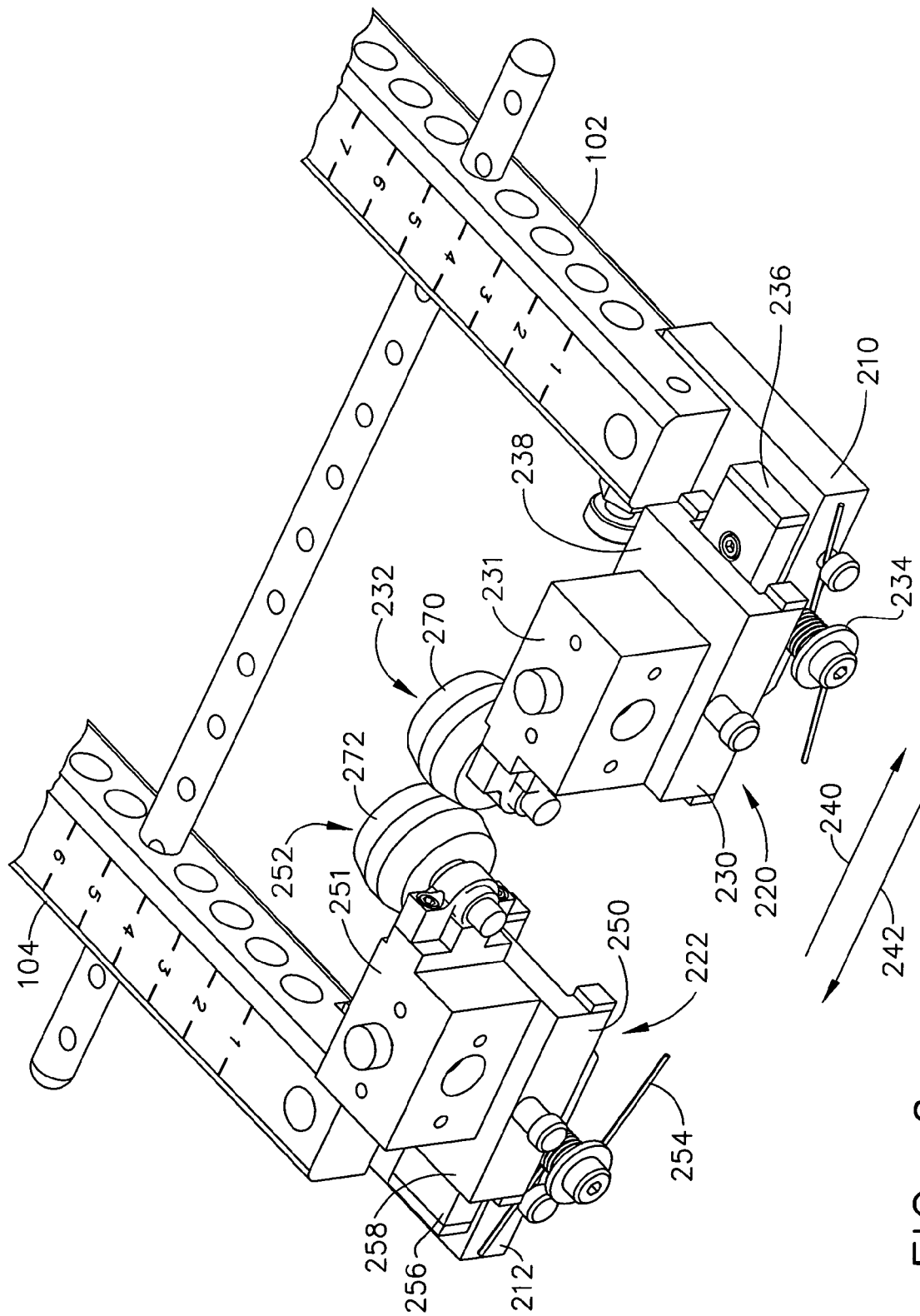
FIG. 6 is a top perspective view of a portion of the probe assembly shown in FIG. 2.

FIG. 6 is a perspective view of ultrasonic transmitter assembly 220 and ultrasonic receiver assembly 222. In the exemplary embodiment, ultrasonic transmitter assembly 220 includes a linear ball slide assembly 230 that is coupled to first mounting plate 210, an ultrasonic transmitter holder 231 that is coupled to linear ball slide assembly 230, an ultrasonic transmitter 232 that is coupled to ultrasonic transmitter holder 231, and a tension device 234, such as a spring for example, that is coupled between ball slide assembly 230 and first mounting plate 210. More specifically, ball slide assembly 230 includes a rail 236 that is coupled to first mounting plate 210, and a slider 238 that is slidably coupled to rail 236 such that slider 238 is movable in either a first direction 240 and/or a second direction 242. More specifically, when an operator moves slider 238 in first direction 240, tension device 234 is compressed. Alternatively, when an operator releases slider 238, tension device 234 automatically moves slider 238 in direction 242.

In the exemplary embodiment, ultrasonic receiver assembly 222 includes a linear ball slide assembly 250 that is coupled to second mounting plate 212, an ultrasonic receiver holder 251 that is coupled to linear ball slide assembly 250, an ultrasonic receiver 252 that is coupled to ultrasonic receiver holder 251, and a tension device 254, such as a spring for example, that is coupled between ball slide assembly 250 and second mounting plate 212. More specifically, ball slide assembly 250 includes a rail 256 that is coupled to second mounting plate 212, and a slider 258 that is slidably coupled to rail 256 such that slider 258 is movable in either first direction 240 and/or second direction 242. More specifically, when an operator moves slider 258 in second direction 242, tension device 254 is compressed. Alternatively, when an operator releases slider 258, tension device 254 automatically moves slider 258 in direction 240. Accordingly, ultrasonic transmitter assembly 220 and ultrasonic receiver assembly 222 are biased towards each other. In the exemplary embodiment, linear ball slide assemblies 230 and 250 are available from American Linear Manufacturers of Westbury N.Y., for example.

In the exemplary embodiment, ultrasonic transmitter 232 and ultrasonic receiver 252 each include a substantially circular roller assembly 270 and 272, respectively that facilitates moving ultrasonic transmitter 232 and ultrasonic receiver 252 along a surface of component 52 during the inspection procedure. Moreover, and in the exemplary embodiment, ultrasonic transmitter 232 and ultrasonic receiver 252 are each rotatable approximately ninety degrees to facilitate ultrasonic transmitter 232 and ultrasonic receiver 252 moving in a substantially vertical and/or a substantially horizontal direction with respect to component 52. Additionally, ultrasonic transmitter 232 and ultrasonic receiver 252 are each electrically coupled to data acquisition/control system 62.

In operation, ultrasonic transmitter 232 transmits ultrasonic pulses through component 52 which are received by ultrasonic receiver 252. Data acquisition/control system 62 receives the information form ultrasonic receiver 252 and stores the information in a memory such as memory 80, for example. Ultrasonic transmitter 232 and ultrasonic receiver 252 are moved, such as along a vertical or horizontal path, while scanning a region of interest (ROI) of component 52. More specifically, electrical signals generated by ultrasonic receiver 252 are received by data acquisition/control system 62 over a data communications link 280 and are either stored in memory 80 or recorder 84. The data collected by data acquisition/control system 62 is then utilized to generate at least one image of component 52.

Figure 7:
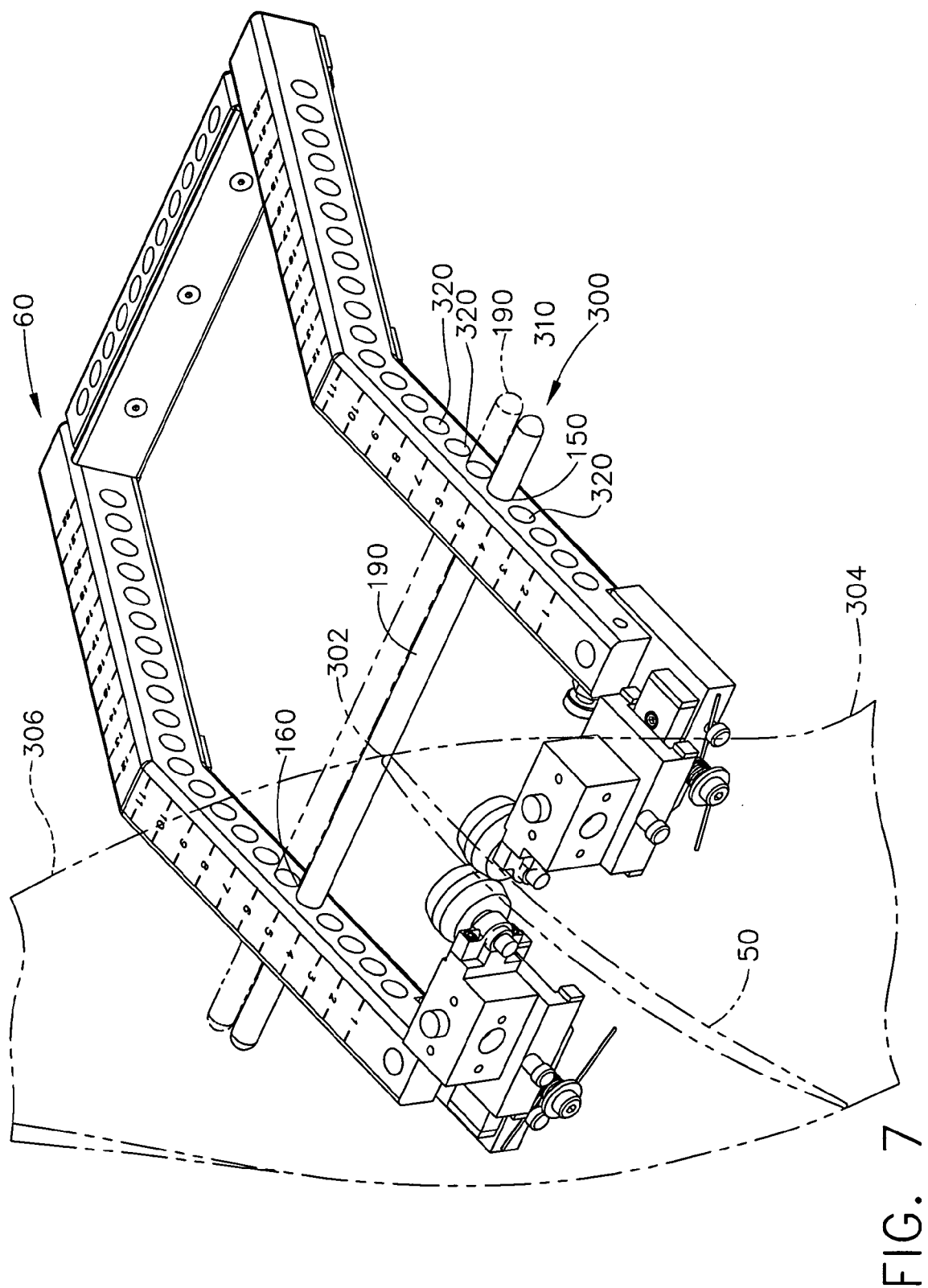
FIG. 7 is a top perspective view of the probe assembly shown in FIG. 2 in a first operational configuration.

FIG. 7 illustrates probe assembly 60 arranged to conduct a vertical scan of component 50. For example, and referring to FIG. 7, probe assembly 60 is configured in a first arrangement such that component 50 can be inspected along a vertical axis. Accordingly, to inspect component 50 along a vertical axis, inspection bar 190 is inserted through first opening 150, and through second opening 160 both positioned at a first inspection point 300. Probe assembly 60 is then positioned around component 50 until a rear edge 302 of component 50 contacts inspection bar 190. Roller assemblies 270 and 272 are positioned to facilitate moving probe assembly 60 along a substantially vertical path. Probe assembly 60 is then moved from a lower edge 304 of component 50 to an upper edge 306 of component 50 while approximately simultaneously transmitting data to system 62. Moreover, ultrasonic waves, transmitted by transmitter 220, are transmitted through component 50, and received by receiver 220. The data is then transmitted from receiver 220 to system 62, wherein an image is generated of the component. The generated image can then be utilized by an operator to detect any delaminations which may have occurred within the component.

Inspection bar 190 is then inserted through first opening 150, and through second opening 160 both positioned at a second inspection point 310. Probe assembly 60 is then positioned around component 50 until a rear edge 302 of component 50 contacts inspection bar 190. Probe assembly 60 is then moved from a lower edge 304 of component 50 to an upper edge 306 of component 50 while approximately simultaneously transmitting data to system 62. In the exemplary embodiment, inspection bar 190 is repositioned at a plurality of inspection points 320, spaced at approximately one inch increments, until an exterior surface of component 50 has been substantially scanned in the vertical direction utilizing probe assembly 60.

Figure 8:
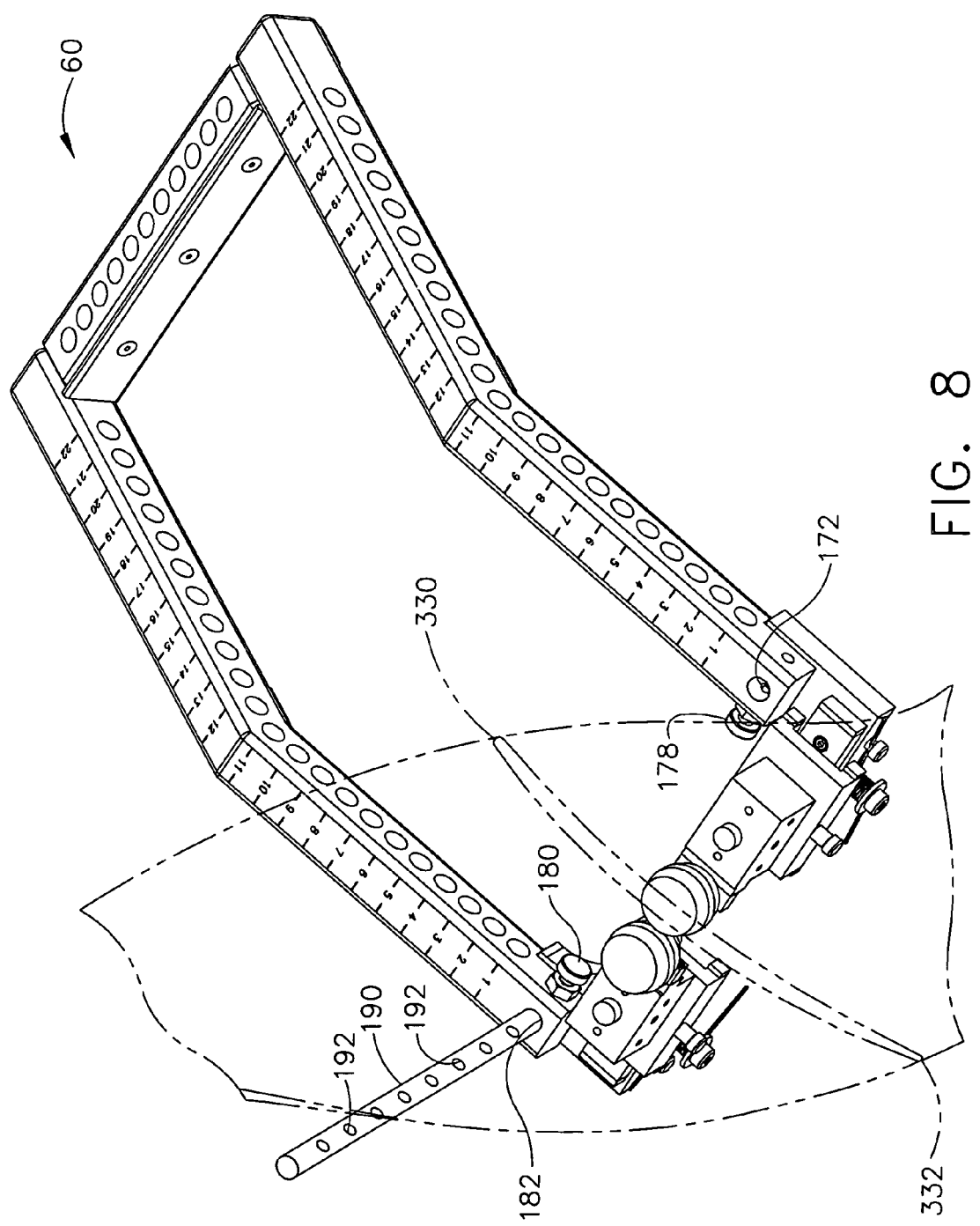
FIG. 8 is a top perspective view of the probe assembly shown in FIG. 2 in a second operational configuration.

FIG. 8 illustrates probe assembly 60 arranged to conduct a horizontal scan of component 50. For example, and referring to FIG. 8, probe assembly 60 is configured in a second arrangement such that component 50 can be inspected along a horizontal axis. Accordingly, to inspect component 50 along a horizontal axis, inspection bar 190 is inserted through at least one of opening 172 or opening 182. More specifically, inspection bar 190 is inserted through one of openings 172 or 182 until a desired opening 192 extending through inspection bar 190 is at a desired position, i.e. inspection bar 190 is positioned at a desired height from the gas turbine engine outer casing. At least one of retaining pins 178 or 180 is then inserted at least partially opening 192 to facilitate securing inspection bar 190 to probe assembly 60. Roller assemblies 270 and 272 are then re-positioned, i.e. rotated approximately ninety degrees, to facilitate moving probe assembly 60 along a substantially horizontal path.

Probe assembly 60 is then positioned around component 50 to facilitate moving probe assembly 60 along a substantially horizontal path. Probe assembly 60 is then moved from a first side 330 of component 50 to a second side 332 of component 50 while approximately simultaneously transmitting data to system 62.

Inspection bar 190 is then inserted through a second opening 192, which are spaced in approximately one inch increments along a length of inspection bar 190. Probe assembly 60 is then moved from a first side 330 of component 50 to a second side 332 of component 50 while approximately simultaneously transmitting data to system 62. In the exemplary embodiment, inspection bar 190 is repositioned at a plurality of points 192 until an exterior surface of component 50 has been substantially scanned in the horizontal direction utilizing probe assembly 60.

The above-described methods and apparatus provide a cost-effective and reliable means to facilitate reducing the amount time needed to perform an ultrasonic inspection on a component under test. Specifically, the method and apparatus described herein facilitates allowing an operating to perform an ultrasonic inspection of a component that is preferably coupled within the gas turbine engine, utilizing a handheld inspection apparatus. In the exemplary embodiment, the apparatus is reconfigurable to scan the component in either a vertical or horizontal direction to ensure that the entire component has been scanned.

More specifically, described herein is an apparatus and test procedure utilized to determine when a delamination has occurred within a gas turbine engine component, such as a gas turbine engine blade. The test is accomplished by using an ultrasonic instrument to monitor the ultrasonic signals, two probes that transmit and receive the ultrasonic signals and an inspection fixture to position the probes on the blade. Once the probes are installed on the fixture, the blade is positioned in-between the probes. The sound is transmitted from one probe, travels through the blade and received by the second probe on the other side of the blade.

In the exemplary embodiment, probe assembly 60 is a dry coupled inspection system, i.e. couplant is not used between the probe and blade to transmit the sound, to facilitate reducing inspection and clean-up time. During operation, if a delamination in the blade is detected, the sound will be blocked and will not be received by the second probe as indicated on the ultrasonic instrument. The fixture has two spring-loaded ball slides that provide probe pressure for good surface contact and to allow movement for the wide variety of blade contours. The fixture provides either vertical or horizontal scans for good coverage in both inspection zones. An indexing device, i.e. the inspection bar, is incorporated for both the vertical and horizontal scans to allow consistent inspection coverage.

Exemplary embodiments of a portable ultrasonic inspection system are described above in detail. The systems are not limited to the specific embodiments described herein, but rather, components of each system may be utilized independently and separately from other components described herein. Each system component can also be used in combination with other system components. More specifically, although the methods and apparatus herein are described with respect to aircraft engine parts, it should be appreciated that the methods and apparatus can also be applied to a wide variety of components used within a steam turbine, a nuclear power plant, an automotive engine, or to inspect any mechanical component.

While the invention has been described in terms of various specific embodiments, those skilled in the art will recognize that the invention can be practiced with modification within the spirit and scope of the claims.

What is claimed is:

1. A method for inspecting a gas turbine engine component, said method comprising:
   positioning an ultrasonic probe assembly proximate to a surface of the component, said ultrasonic probe assembly including a body portion and an inspection bar;
   coupling the inspection bar to the body portion such that the inspection bar is substantially parallel to a first axis, wherein the first axis is substantially perpendicular to an upper surface of the body portion;
   moving the ultrasonic probe assembly along a second axis while generating ultrasonic data of the component, wherein the second axis is substantially perpendicular to the first axis;
   coupling the inspection bar to the body portion such that the inspection bar is substantially aligned with the second axis;
   moving the ultrasonic probe assembly along the first axis while generating ultrasonic data of the component; and
   utilizing the generated data to reconstruct an image of the component.

2. A method in accordance with claim 1 further comprising utilizing the reconstructed image to detect at least one delamination within the component.

3. A method in accordance with claim 1 further comprising:
   indexing the inspection bar from a first position to a second position, wherein the inspection bar is substantially aligned with the first axis; and
   moving the ultrasonic probe assembly along the second axis while generating ultrasonic data of the component.

4. A method in accordance with claim 1 further comprising:
   indexing the inspection bar from a first position to a second position, wherein the inspection bar is substantially aligned with the second axis; and
   moving the ultrasonic probe assembly along the first axis while generating ultrasonic data of the component.

5. A method in accordance with claim 1 wherein the ultrasonic probe assembly further comprises an ultrasonic transmitter coupled to a first end of the body portion and an ultrasonic receiver coupled to a second end of the body portion, said method further comprising:
   utilizing the ultrasonic transmitter to transmit a plurality of ultrasonic waves through the component under test; and
   utilizing the ultrasonic receiver to receive at least a portion of the ultrasonic waves transmitted through said component under test.

6. A method in accordance with claim 5 further comprising transmitting the received waveforms from the receiver to a data acquisition and control system to facilitate generating an image of the component.

7. A method in accordance with claim 5 wherein the ultrasonic probe assembly further includes a first ball slide assembly coupled to the first end of the body portion, the ultrasonic transmitter coupled to the first ball slide assembly and a second ball slide assembly coupled to the second end of the body portion, the ultrasonic receiver coupled to the second ball slide assembly, said method further comprising moving the first and second ball slide assemblies until the ultrasonic transmitter and ultrasonic receiver are positioned proximate to a surface of the component.

8. A method in accordance with claim 7 wherein said ultrasonic probe assembly further includes a first roller assembly coupled to the first ball slide assembly, and a second roller assembly coupled to the second ball slide assembly, said method further comprising:
   moving the first and second roller assemblies to a first position to perform a first scan of the component, the first scan is performed substantially parallel to the second axis; and moving the first and second roller assemblies to a second position to perform a second scan of the component, the first position offset from the second position by approximately ninety degrees, the second scan performed substantially parallel to the first axis.

9. A method in accordance with claim 7 wherein the first and second ball slide assemblies each include a biasing mechanism that is configured to hold the ultrasonic transmitter and ultrasonic receiver next to a surface of the component during testing.

10. A method in accordance with claim 1 further comprising:
providing a gas turbine engine that includes a least one gas turbine rotor blade;
positioning the ultrasonic probe assembly proximate to a surface of the gas turbine engine rotor blade; and
moving the ultrasonic probe assembly along at least one of the first axis and the second axis to generate ultrasonic data of the gas turbine engine rotor blade.

11. An ultrasonic probe assembly for inspecting a component, said ultrasonic probe assembly comprising:
a substantially U-shaped body portion comprising a first portion, a second portion, and a third portion coupled to said first and second portions;
an inspection bar coupled to said body portion, said inspection bar configured to contact said component to orient said body portion with respect to said component;
an ultrasonic transmitter coupled to a first end of said body portion and configured to transmit a plurality of ultrasonic waves through said component under test;
an ultrasonic receiver coupled to a second end of said body portion configured to receive at least a portion of said ultrasonic waves transmitted through said component under test; and
a data acquisition system configured to receive data from said ultrasonic receiver and reconstruct an image of said component under test.

12. An ultrasonic probe assembly in accordance with claim 11 wherein said inspection bar is alignable with at least one of a first axis and a second axis, wherein said first axis is substantially perpendicular with respect to an upper surface of said body portion, and said second axis is substantially perpendicular to said first axis.

13. An ultrasonic probe assembly in accordance with claim 12 wherein said first and second portions each comprise a plurality of openings extending therethrough, said inspection bar positioned within at least two of said plurality of openings to facilitate moving said ultrasonic probe assembly in a direction along said first axis, each of said plurality of openings is defined substantially parallel to said second axis.

14. An ultrasonic probe assembly in accordance with claim 12 wherein said first and second portions each comprise at least one opening extending therethrough, said inspection bar positioned within said at least one opening to facilitate moving said ultrasonic probe assembly in direction along said second axis, said at least one opening is defined substantially parallel to said first axis.

15. An ultrasonic probe assembly in accordance with claim 11 further comprising:
a first ball slide assembly coupled to said first end of said body portion, said ultrasonic transmitter coupled to said first ball slide assembly and configured to transmit a plurality of ultrasonic waves through said component under test; and
a second ball slide assembly coupled to said second end of said body portion, said ultrasonic receiver coupled to said second ball slide assembly and configured to receive at least a portion of said ultrasonic waves transmitted through said component under test.

16. An ultrasonic probe assembly in accordance with claim 15 further comprising:
a first roller assembly coupled to said first ball slide assembly; and
a second roller assembly coupled to said second ball slide assembly.

17. An ultrasonic probe assembly in accordance with claim 16, wherein each of said first and second roller assemblies are reconfigurable from a first position to a second position to facilitate moving said ultrasonic probe assembly in at least one of a direction that is substantially perpendicular and a direction that is substantially parallel with respect to an upper surface of found body portion.

18. An ultrasonic probe assembly in accordance with claim 15 wherein said first and second ball slide assemblies each include a biasing mechanism such that said first and second ball slide assemblies are biased towards said component.

19. An ultrasonic probe assembly in accordance with claim 11 wherein said component is a gas turbine engine fan blade, said ultrasonic probe assembly configured to scan said fan blade while said fan blade is installed in a gas turbine engine.

20. An ultrasonic probe assembly in accordance with claim 11 wherein said body portion comprises a substantially V-shaped cross-sectional profile.

\* \* \* \* \*

UNITED STATES PATENT AND TRADEMARK OFFICE
CERTIFICATE OF CORRECTION

PATENT NO. : 7,313,961 B2  
APPLICATION NO. : 11/114316  
DATED : January 1, 2008  
INVENTOR(S) : Tenley et al.

Page 1 of 1

It is certified that error appears in the above-identified patent and that said Letters Patent is hereby corrected as shown below:

In Claim 14, column 10, line 5, delete "in direction" and insert therefor -- in a direction --.
In Claim 17, column 10, line 32, delete "found" and insert therefor -- said --.

Signed and Sealed this

Twenty-fourth Day of June, 2008

JON W. DUDAS  
*Director of the United States Patent and Trademark Office*